United States Patent [19]

Hsu

[11] Patent Number: 4,701,561
[45] Date of Patent: Oct. 20, 1987

[54] SEPARATION OF ALDEHYDES FROM KETONES VIA ACID-CATALYZED CYCLOTRIMERIZATION OF THE ALDEHYDE

[75] Inventor: Wen-Liang Hsu, Copley, Ohio

[73] Assignee: The Goodyear Tire & Rubber Company, Akron, Ohio

[21] Appl. No.: 25,428

[22] Filed: Mar. 13, 1987

[51] Int. Cl.$^4$ .............................................. C07C 45/78
[52] U.S. Cl. .................................... 568/492; 568/340; 568/410
[58] Field of Search ........................ 568/340, 410, 492

[56] References Cited

U.S. PATENT DOCUMENTS 4,523,038  6/1985  Scott ..................................... 568/492

FOREIGN PATENT DOCUMENTS 501374  4/1954  Canada ................................ 568/410

Primary Examiner—Werren B. Lone
Attorney, Agent, or Firm—D. O. Nickey

[57] ABSTRACT

This invention is directed to the discovery that a mixture of aldehydes and ketones where the boiling points of the aldehyde and the ketone are very close can be easily separated through the acid-catalyzed cyclotrimerization of the aldehyde and the subsequent distillation of the ketone and unreacted aldehyde from the reaction mixture. The trimerized aldehyde is cracked back to the starting aldehyde in high purity at elevated temperatures in the presence of an acid catalyst.

10 Claims, No Drawings

SEPARATION OF ALDEHYDES FROM KETONES VIA ACID-CATALYZED CYCLOTRIMERIZATION OF THE ALDEHYDE

TECHNICAL FIELD

This invention relates to the discovery that ketones and aldehydes having close boiling points can be readily separated through the acid-catalyzed cyclotrimerization of the aldehyde and the subsequent distillative separation of the ketone and unreacted aldehyde from the trimerized aldehyde. The cyclotrimerized aldehyde can thereafter be "cracked-back" to the starting aldehyde easily and efficiently.

BACKGROUND ART

Numerous methods have been developed over the years to produce isoprene. One method described in U.S. Pat. No. 4,524,233, herein incorporated by reference, discloses the dehydration reaction of 2-methylbutanal (2MBA) over a dehydration catalyst such as boron phosphate to yield isoprene. As disclosed in U.S. Pat. No.4,524,233, a major by-product of the 2MBA dehydration is methylisopropylketone (MIPK). For the economical operation of a process as described in this U.S. patent, it will be required to recycle the 2MBA that is not converted to MIPK or isoprene, back to the dehydration reactor.

The close boiling points of 2MBA (90°–92° C.) and MIPK (92°–94° C.) make separation by distillation difficult. A separation of two compounds having close boiling points is known to those skilled in this art to present extreme difficulties.

The inventor herein has unexpectedly found that a mixture of aldehyde such as 2MBA and a ketone such as MIPK can be separated after acid-catalyzed cyclotrimerization of the aldehyde. The ketone and unreacted aldehyde are distilled away from the cyclotrimerized aldehyde easily and efficiently and thereafter, the cyclotrimerized aldehyde can be catalytically reconverted to the starting aldehyde in high purity. None of the prior art suggests or discloses this unique approach to the separation of close boiling aldehydes and ketones.

U.S. Pat. No. 4,163,696 is concerned with a distillation process for the recovery of methylisobutyl ketone. This patent discloses an azeotropic distillation process for separating toluene from methylisobutyl ketone in a spent liquor mixture. A toluene azeotrope former, preferably methanol, is added to the liquor in an amount sufficient to form an azeotrope with all the toluene present in the mixture.

It is known that when catalyzed by acids, low molecular weight aldehydes add to each other to form trimers. See, for example, Bevington, J C, Quart. Rev. (London) 6, 141 (1952). Although these cyclic acetals are stable to bases, they can be converted back to monomeric aldehydes by acids with heat. The following is a structural representation of the acid-catalyzed cyclotrimerization of an aldehyde:

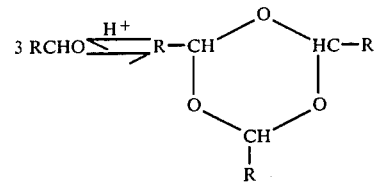

wherein R can be a hydrocarbon radical of 1 to 16 carbon atoms.

These acid-catalyzed cyclotrimerizations of the aldehyde do not affect the ketone or other nonaldehyde components. The trimers have substantially higher boiling points than their monomers.

A portion of the instant invention resides in the application of this unique property of aldehydes to the specific problem of separating close boiling mixtures of an aldehyde and a ketone. The unique process of this invention provides a means for separating these close boiling components. The aldehyde is selectively trimerized to a high boiling trimer at low temperatures by an insoluble solid acid catalyst. After removing the catalyst by filtration or other means, the aldehyde trimer is separated from the ketone and unreacted aldehyde by stripping or distilling the low boiling point compounds from the filtrate. The desired aldehyde is then recovered by heating its trimer with a solid acid catalyst to convert it back to the monomeric aldehyde species. The thus obtained aldehyde is of high purity.

DISCLOSURE OF THE INVENTION

There is disclosed a process for the separation of an aldehyde of 3 to 16 carbon atoms from a close boiling mixture, said process comprising (1) contacting the aldehyde containing mixture with a solid acid catalyst at a temperature from 0 to 35° C. to cyclotrimerize a major portion of the aldehyde contained in the mixture; (2) distill the unreacted aldehyde and other components of the mixture from the high boiling cyclotrimerized aldehyde in the absence of the catalyst: and (3) contacting the thus isolated cyclotrimerized aldehyde with an acid catalyst at elevated temperatures to produce essentially pure aldehyde.

There is also disclosed a process for the separation of 2-methylbutanal from a mixture comprising 5 to 85 parts by weight of methylisopropylketone and from 5–95 parts by weight of 2-methylbutanal, said process comprising contacting the mixture with a solid acid catalyst at a temperature from 0°–35° C. so that the aldehyde is cyclotrimerized; distillative separation of the methylisopropylketone and unreacted aldehyde from the cyclotrimerized 2-methylbutanal; contacting the cyclotrimerized aldehyde with an acid catalyst at elevated temperatures to produce essentially pure aldehyde.

The composition of the effluent from the 2MBA to diene dehydration reaction contains isoprene, MIPK, 2MBA and water in addition to other minor by-products. A typical single pass effluent analysis from the dehydration reaction of 2MBA to isoprene contains about 2 to 3% by weight MIPK, however, as the 2MBA/MIPK is recycled, the level of MIPK increases to a point where the yield of isoprene is greatly diminished per pass over the catalyst. In order to increase the yield of isoprene per pass, the level of MIPK in the recycle must be kept to a minimum.

In a simple fractionation of the effluent from the dehydration reactor, the isoprene is easily removed leaving essentially a mixture of 2MBA and MIPK to be recycled to the dehydration reactor. It is advantageous in the aldehyde to diene dehydration that the aldehyde be as pure as possible thus insuring the highest level of isoprene production, since the presence of ketone in the aldehyde feed has been shown to be detrimental to the efficient production of the diene.

Products obtained from 2-methylbutanal (2MBA) dehydration include isoprene; light by-products, such as 2-methyl-1-butene, 2-methyl-2-butene and the like; with methylisopropyl ketone (MIPK) as the major by-product. Isoprene and the light by-products are easily separated by distillation. MIPK is known to be more reluctant to dehydrate than 2MBA and to recycle the unreacted 2MBA, MIPK should be removed to avoid the dilution of the aldehyde feed. It should be appreciated that it would be very costly to physically separate the ketone from the aldehyde by distillation due to their very similar boiling points of 92°–93° C. for 2MBA and 94°–95° C. for MIPK. Through the process of this invention, essentially pure 2MBA is separated from the mixture by selective cyclotrimerization of the 2MBA. The process described and claimed herein, when incorporated into the aldehyde to diene process can be depicted as follows:

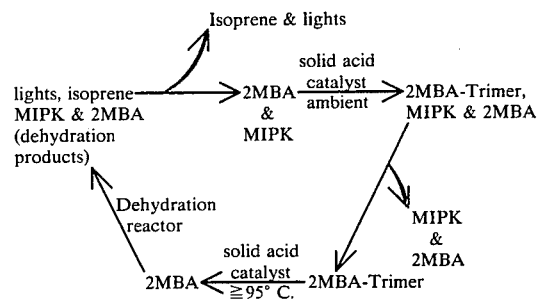

The process of this invention provides a novel and unobvious method which allows for the efficient and facile separation of an aldehyde from a close boiling ketone. The process of this invention is unique and efficient since the aldehyde trimerizes at low temperature (room temperature or lower) in the presence of an acid catalyst, preferably a solid acid catalyst. In contrast, the ketone, such as MIPK, will not react under the same conditions. The trimerization of the aldehyde results in a compound such as 2,4,6-tri-sec-butyl-1,3,5-trioxane and these cyclic compounds usually have very high boiling points (sometimes in excess of 300° C.) and are thermally stable in the absence of an acid catalyst. After distillative separation of high boiling timer from the mixture the trimer can be easily and quantitatively cracked back to the starting aldehyde at an elevated temperature in the presence of an acid catalyst.

Representative of the acid catalysts that are useful in the process of the invention are any acidic catalyst; however, insoluble solid acid catalysts, such as Nafion (polymer bound perfluorosulfonic acid), BPO$_4$, H$_3$PO$_4$ on SiO$_2$, Amberlyst 15 and the like are both useful and adequate. The solid acid catalysts are preferred in the process of this invention due to the ease of separation by filtration, their recyclability and suitability for a continuous process.

The process of this invention may be conducted on a batch basis or in a continuous process.

BEST MODE

The following Examples are intended to illustrate and not to limit the scope of the present invention.

EXAMPLES 1 and 2

To a reaction flask fitted with a stirrer, a condenser and a nitrogen inlet was charged 200 ml of a 7 to 1 mixture by volume of 2-methylbutanal and MIPK and 5 g of the solid acid catalyst Nafion. The mixture was stirred under an atmosphere of nitrogen for 48 hours at room temperature or 45° C. (as indicated). Samples of the reaction mixture were taken at different times and submitted for analysis. The reaction mixture was then filtered to remove the acid catalyst. The filtrate was returned to the reaction vessel fitted with a distillation column and heated.

The low boiling MIPK and unreacted 2MBA was taken overhead to yield essentially pure cyclotrimerized 2MBA in the pot. After all the MIPK and 2MBA had distilled off, 5 gms of Nafion acid catalyst was charged to the reactor. The quantitative decomposition of the trimer to free aldehyde began immediately. Pure 2MBA was collected overhead as the pot temperature was kept at about 100° C.

Table I sets out the temperature, hours the 2MBA/MIPK was heated to produce the trimer and the percentage of 2MBA that had trimerized. The % trimer was determined by NMR spectroscopy.

TA8LE I

| 2MBA Trimer Formation from a 7:1 2MBA/MIPK Mixture Catalyzed by a Solid Acid Catalyst | | |
|---|---|---|
| | Reaction Time (Hours) | % of 2MBA in Mixture Trimerized |
| Ex 1 - Room Temp. | 1 | 37 |
| | 3 | 53 |
| | 5 | 62 |
| | 19 | 77 |
| | 22 | 75 |
| | 24 | 76 |
| | 28 | 76 |
| | 44 | 77 |
| | 48 | 77 |
| Ex 2 - 45° C. | 1 | 28 |
| | 3 | 37 |
| | 5 | 37 |
| | 19 | 32 |
| | 22 | 35 |
| | 24 | 34 |
| | 28 | 33 |
| | 44 | 32 |
| | 48 | 33 |

From the data in Table I it is apparent that room termperature trimerization of the aldehyde is favored over the 45° C. the timer is less stable in the presence of the catalyst and reverts back to the starting aldehyde.

As described above, the catalyst was separated, the MIPK and unreacted 2MBA, was flashed off and the cyclotrimerized aldehyde cracked back to the starting aldehyde in the presence of the acid catalyst at temperatures from 90°–100° C.

EXAMPLE 3

Using the apparatus and procedure of Examples 1 and 2, except that the solid acid catalyst Amberlyst 15 TM (Trademark for Rohm & Haas' sulfonated styrene-divinylbenzene resin) was used and the volume ratio of 2MBA to MIPK was 3:1. After 27 hours at room temperature 76% by weight of the 2MBA had trimerized.

EXAMPLE 4

Using the apparatus and procedure of Example 1, pure MIPK was contacted with Nafion and Amerlyst-15 ™ to determine if any reaction took place. After 24 hours at room temperature no reaction was detected with either catalyst.

EXAMPLE 5

A down flow continuous reactor was constructed so that liquid 2MBA was passed through a bed of Nafion catalyst at room temperature and at LHSV's (liquid hourly space velocities) of 2.25 and 4.5. 70-75% of the 2MBA was trimerized using this procedure which simulates a continuous reaction system.

EXAMPLE 6

Using trimerized 2MBA that was prepared previously, Nafion and BPO$_4$ were used to decompose the trimer to 2MBA. In both cases 100% conversion of the trimer to 2MBA was realized in about 2 hours at 100° C.

INDUSTRIAL APPLICABILITY

The process of this invention provides for the efficient and economical separation of a close boiling aldehyde from a ketone. The trimerization of aldehydes is known; however, the instant invention provides a nondestructive process for the separation of aldehydes from ketones via trimerization of the aldehyde. The utilization of an insoluble acid catalyst to facilitate product separation is both unique and unobvious. Those skilled in this art will readily appreciate the chemical processing advantages and economic advantages that can be realized through utilization of the process described and claimed herein.

What is claimed is:

1. A process for the separation of an aldehyde of 3 to 16 carbon atoms from a close boiling mixture, said process comprising:
   (1) contacting the aldehyde containing mixture with a solid acid catalyst at a temperature from 0 to 35° C. to cyclotrimerize a major portion of the aldehyde contained in the mixture;
   (2) distill the unreacted aldehyde and other components of the mixture from the high boiling cyclotrimerized aldehyde in the absence of the catalyst; and
   (3) contacting the thus isolated cyclotrimerized aldehyde with a acid catalyst at elevated temperatures to produce essentially pure aldehyde.

2. A process for the separation of 2-methylbutanal from a mixture comprising 5 to 85 parts by weight of methylisopropylketone and from 5-95 parts by weight of 2-methylbutanal; said process comprising contacting the mixture with a solid acid catalyst at a temperature from 0°-35° C. so that the aldehyde is cyclotrimerized; distillative separation of the methylisopropylketone and unreacted aldehyde from the cyclotrimerized 2-methylbutanal; contacting the cyclotrimerized aldehyde with an acid catalyst at elevated temperatures to produce essentially pure aldehyde.

3. A process as specified in claim 1 wherein the aldehyde is 2-methylbutanal and the ketone is MIPK.

4. A process as specified in claim 1 wherein the acid catalyst is selected from the group of catalysts consisting of polymer bound perfluorosulfonic acid, BPO$_4$, H$_3$PO$_4$ on SiO$_2$ and sulfonated styrene-divinylbenzene resin.

5. A process as specified in claim 1 wherein the temperature of the cyclotrimerization is from 10° C. to 30° C.

6. A process as specified in claim 1 wherein the decomposition of the cyclotrimerized aldehyde is conducted in the presence of a solid acid catalyst temperature of 95° C. to 100° C.

7. A process according to claim 2 wherein the mixture consists of 10-50 parts by weight of methylisopropylketone and 50-90 parts by weight of 2-methylbutanal.

8. A process according to claim 2 wherein the acid catalyst is selected from the group of catalysts consisting of polymer bound perfluorosulfonic acid, BPO$_4$, H$_3$PO$_4$ on SiO$_2$ and sulfonated styrene-divinylbenzene resin.

9. A process according to claim 2 wherein the temperature of the cyclotrimerization is from 10° C. to 30° C.

10. A process according to claim 2 wherein the decomposition of the cyclotrimerized aldehyde is conducted in the presence of a solid acid catalyst temperature of 95° C. to 100° C.

* * * * *